(12) United States Patent
Takahashi et al.

(10) Patent No.: US 8,338,361 B2
(45) Date of Patent: Dec. 25, 2012

(54) FRAGRANCE COMPOSITION

(75) Inventors: Fumikazu Takahashi, Haga-gun (JP); Kazuyuki Fukuda, Sumida-ku (JP); Yasushi Takimura, Haga-gun (JP); Takahiro Asada, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/143,118

(22) PCT Filed: Jan. 13, 2010

(86) PCT No.: PCT/JP2010/050738
§ 371 (c)(1),
(2), (4) Date: Jul. 1, 2011

(87) PCT Pub. No.: WO2010/082684
PCT Pub. Date: Jul. 22, 2010

(65) Prior Publication Data
US 2011/0269664 A1  Nov. 3, 2011

(30) Foreign Application Priority Data

Jan. 13, 2009 (JP) ................................. 2009-004854
Jan. 13, 2009 (JP) ................................. 2009-004877

(51) Int. Cl.
*A61Q 13/00* (2006.01)
(52) U.S. Cl. ........................................................ 512/11
(58) Field of Classification Search ................. 512/11
See application file for complete search history.

(56) References Cited

U.S. PATENT DOCUMENTS

| | | | |
|---|---|---|---|
| 3,681,395 A | 8/1972 | Mookherjee et al. | |
| 4,064,144 A | 12/1977 | Tseng | |
| 5,266,559 A | 11/1993 | Fankhauser et al. | |
| 6,008,185 A * | 12/1999 | Bertram et al. | 512/12 |
| 2003/0055105 A1 * | 3/2003 | Ito et al. | 514/473 |
| 2005/0037037 A1 | 2/2005 | Finke et al. | |
| 2008/0020963 A1 | 1/2008 | Takaoka | |

FOREIGN PATENT DOCUMENTS

| | | |
|---|---|---|
| EP | 0 862 911 A2 | 9/1998 |
| EP | 1 741 706 A1 | 1/2007 |
| FR | 1406122 A | 7/1965 |
| JP | 2-6516 B | 2/1990 |
| JP | B-4-12718 | 3/1992 |
| JP | A-11-192096 | 7/1999 |
| JP | A-2005-065658 | 3/2005 |
| WO | WO 03/038019 A1 | 5/2003 |

OTHER PUBLICATIONS

International Search Report (ISR) for PCT/JP2010/050738, I.A. fd: Jan. 13, 2010, mailed May 25, 2010 from the European Patent Office, Rijswijk, Netherlands.

International Preliminary Report on Patentability (IPRP), Chapter I of the Patent Cooperation Treaty, including the Written Opinion for PCT/JP2010/050738, I.A. fd: Jan. 13, 2010, issued Jul. 19, 2011 from the International Bureau of WIPO, Geneva, Switzerland.
Bersuker, IB et al., "Origin of musk fragrance activity: the electron-topologic approach," New J Chem 15(5):307-320 (1991), Centre National de la Recherche Scientific, Paris, France.
Abe, S, "Macrocyclic Musks, Part I, review on progress from discovery up to now," Perfume No. 96, pp. 19-27 (Sep. 1970), Koryo.
Hinkamp, L et al., "Retroselective conversion of nonactivated CH bonds, VI: Selective ω- to (ω—2)-chlorination of fatty acids by way of adsorption on alumina," Liebigs Ann Chem 1992(6):559-563 (Jun. 1992), Weinheim, New York, Verlag Chemie.
Wright, RH, "The musk odour," Perfumery and Essential Oil Record, 58(9):648-650 (Sep. 1967), G. Street & Co., Ltd., London, England.
Kraft, P. et al., "Stereoselective synthesis of both enantiomers of 13-tetradecanolide by ring enlargement with different chiral building blocks and olfactory comparison with (12$R$)-(+)- and (12$S$)-(−)-12-methyl-13-tridecanolide," Liebigs Ann Chem 1995(8):1409-1414 (Jul. 1995), Weinheim, New York, Verlag Chemie.
Koike, K et al., "Substrate specificity of regiospecific desaturation of aliphatic compounds by a mutant Rhodococcus strain," Biosci Biotechnol Biochem, 64(5):1064-1066 (May 2000), Japan Society for Bioscience, Biotechnology, and Agrochemistry, Tokyo, Japan.
Mosandl, A. et al., "Stereoisomeric Flavor Compounds. 20. Structure and properties of γ-Lactone Enantiomers," J. Agric. Food Chem. 37:413-418 (1989), American Chemical Society, Washington, DC.
Pittet, AO et al., "Synthesis and flavor properties of some alkyl-substituted α-pyrone derivatives," J. Agric. Food Chem. 23:1189-1195 (1975), American Chemical Society, Washington, DC.
Sell, C.S., "On the Unpredictability of Odor," Angew. Chem. Int. Ed. 45: 6254-6261 (2006), Wiley-VCH Verlag GmbH & Co., Weinheim, Germany.

* cited by examiner

*Primary Examiner* — Ling Choi
*Assistant Examiner* — Lanee Reuther
(74) *Attorney, Agent, or Firm* — Sterne, Kessler, Goldstein & Fox P.L.L.C.

(57) ABSTRACT

A novel musk-based fragrance having an excellent musky fragrance is provided. Also provided is a fragrance composition containing, as an active ingredient, a macrocyclic lactone compound represented by the following formula (1): wherein A represents an ethylene group or an ethenylene group; and when A is an ethylene group, R represents an alkyl group having 3 carbon atoms, and n represents an integer from 1 to 6, while when A is an ethenylene group, R represents an alkyl group having 1 to 3 carbon atoms, and n represents an integer from 1 to 6.

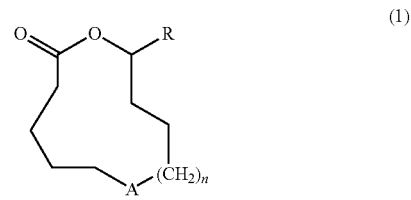

(1)

7 Claims, No Drawings

SEQUENCE LISTING

<160> NUMBER OF SEQ ID NOS: 6

<210> SEQ ID NO 1
<211> LENGTH: 1049
<212> TYPE: PRT
<213> ORGANISM: Bacillus megaterium

```
<400> SEQUENCE: 1

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415
```

-continued

```
Met Met Leu Lys His Phe Asp Phe Glu Asp His Thr Asn Tyr Glu Leu
            420             425             430
Asp Ile Lys Glu Thr Leu Thr Leu Lys Pro Glu Gly Phe Val Val Lys
            435             440             445
Ala Lys Ser Lys Lys Ile Pro Leu Gly Gly Ile Pro Ser Pro Ser Thr
            450             455             460
Glu Gln Ser Ala Lys Lys Val Arg Lys Lys Ala Glu Asn Ala His Asn
465             470             475             480
Thr Pro Leu Leu Val Leu Tyr Gly Ser Asn Met Gly Thr Ala Glu Gly
            485             490             495
Thr Ala Arg Asp Leu Ala Asp Ile Ala Met Ser Lys Gly Phe Ala Pro
            500             505             510
Gln Val Ala Thr Leu Asp Ser His Ala Gly Asn Leu Pro Arg Glu Gly
            515             520             525
Ala Val Leu Ile Val Thr Ala Ser Tyr Asn Gly His Pro Pro Asp Asn
            530             535             540
Ala Lys Gln Phe Val Asp Trp Leu Asp Gln Ala Ser Ala Asp Glu Val
545             550             555             560
Lys Gly Val Arg Tyr Ser Val Phe Gly Cys Gly Asp Lys Asn Trp Ala
            565             570             575
Thr Thr Tyr Gln Lys Val Pro Ala Phe Ile Asp Glu Thr Leu Ala Ala
            580             585             590
Lys Gly Ala Glu Asn Ile Ala Asp Arg Gly Glu Ala Asp Ala Ser Asp
            595             600             605
Asp Phe Glu Gly Thr Tyr Glu Glu Trp Arg Glu His Met Trp Ser Asp
            610             615             620
Val Ala Ala Tyr Phe Asn Leu Asp Ile Glu Asn Ser Glu Asp Asn Lys
625             630             635             640
Ser Thr Leu Ser Leu Gln Phe Val Asp Ser Ala Ala Asp Met Pro Leu
            645             650             655
Ala Lys Met His Gly Ala Phe Ser Thr Asn Val Val Ala Ser Lys Glu
            660             665             670
Leu Gln Gln Pro Gly Ser Ala Arg Ser Thr Arg His Leu Glu Ile Glu
            675             680             685
Leu Pro Lys Glu Ala Ser Tyr Gln Glu Gly Asp His Leu Gly Val Ile
            690             695             700
Pro Arg Asn Tyr Glu Gly Ile Val Asn Arg Val Thr Ala Arg Phe Gly
705             710             715             720
Leu Asp Ala Ser Gln Gln Ile Arg Leu Glu Ala Glu Glu Glu Lys Leu
            725             730             735
Ala His Leu Pro Leu Ala Lys Thr Val Ser Val Glu Glu Leu Leu Gln
            740             745             750
Tyr Val Glu Leu Gln Asp Pro Val Thr Arg Thr Gln Leu Arg Ala Met
            755             760             765
Ala Ala Lys Thr Val Cys Pro Pro His Lys Val Glu Leu Glu Ala Leu
            770             775             780
Leu Glu Lys Gln Ala Tyr Lys Glu Gln Val Leu Ala Lys Arg Leu Thr
785             790             795             800
Met Leu Glu Leu Leu Glu Lys Tyr Pro Ala Cys Glu Met Lys Phe Ser
            805             810             815
Glu Phe Ile Ala Leu Leu Pro Ser Ile Arg Pro Arg Tyr Tyr Ser Ile
            820             825             830
Ser Ser Ser Pro Arg Val Asp Glu Lys Gln Ala Ser Ile Thr Val Ser
```

```
                835              840              845
Val Val Ser Gly Glu Ala Trp Ser Gly Tyr Gly Glu Tyr Lys Gly Ile
        850              855              860

Ala Ser Asn Tyr Leu Ala Glu Leu Gln Glu Gly Asp Thr Ile Thr Cys
865              870              875              880

Phe Ile Ser Thr Pro Gln Ser Glu Phe Thr Leu Pro Lys Asp Pro Glu
            885              890              895

Thr Pro Leu Ile Met Val Gly Pro Gly Thr Gly Val Ala Pro Phe Arg
            900              905              910

Gly Phe Val Gln Ala Arg Lys Gln Leu Lys Glu Gln Gly Gln Ser Leu
        915              920              925

Gly Glu Ala His Leu Tyr Phe Gly Cys Arg Ser Pro His Glu Asp Tyr
930              935              940

Leu Tyr Gln Glu Glu Leu Glu Asn Ala Gln Ser Glu Gly Ile Ile Thr
945              950              955              960

Leu His Thr Ala Phe Ser Arg Met Pro Asn Gln Pro Lys Thr Tyr Val
                965              970              975

Gln His Val Met Glu Gln Asp Gly Lys Lys Leu Ile Glu Leu Leu Asp
            980              985              990

Gln Gly Ala His Phe Tyr Ile Cys Gly Asp Gly Ser Gln Met Ala Pro
        995              1000             1005

Ala Val  Glu Ala Thr Leu Met  Lys Ser Tyr Ala Asp  Val His Gln
1010              1015              1020

Val Ser  Glu Ala Asp Ala Arg  Leu Trp Leu Gln Gln  Leu Glu Glu
1025              1030              1035

Lys Gly  Arg Tyr Ala Lys Asp  Val Trp Ala Gly
1040              1045

<210> SEQ ID NO 2
<211> LENGTH: 261
<212> TYPE: PRT
<213> ORGANISM: Bacillus subtilis

<400> SEQUENCE: 2

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
```

```
                    165                 170                 175
Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 3
<211> LENGTH: 28
<212> TYPE: DNA
<213> ORGANISM: Artificial
<220> FEATURE:
<223> OTHER INFORMATION: Synthesized

<400> SEQUENCE: 3
gcaggatcca tgacaattaa agaaatgc                                    28

<210> SEQ ID NO 4
<211> LENGTH: 27
<212> TYPE: DNA
<213> ORGANISM: Artificial
<220> FEATURE:
<223> OTHER INFORMATION: Synthesized

<400> SEQUENCE: 4
gctgaattct tacccagccc acacgtc                                     27

<210> SEQ ID NO 5
<211> LENGTH: 29
<212> TYPE: DNA
<213> ORGANISM: Artificial
<220> FEATURE:
<223> OTHER INFORMATION: Synthesized

<400> SEQUENCE: 5
gctgaattca ggaggatgta tatgtatcc                                   29

<210> SEQ ID NO 6
<211> LENGTH: 29
<212> TYPE: DNA
<213> ORGANISM: Artificial
<220> FEATURE:
<223> OTHER INFORMATION: Synthesized

<400> SEQUENCE: 6
gctctcgaga ttaaccgcgg cctgcctgg                                   29
```

FRAGRANCE COMPOSITION

REFERENCE TO SEQUENCE LISTING SUBMITTED ELECTRONICALLY

The content of the electronically submitted substitute sequence listing, file name sequencelisting_ascii.txt; size 12,440 bytes; and date of creation Jun. 22, 2011, filed herewith, is incorporated herein by reference in its entirety.

FIELD OF THE INVENTION

The present invention relates to a fragrance composition containing a macrocyclic lactone compound as an active ingredient.

BACKGROUND OF THE INVENTION

At present, natural musk fragrances are not easily available from the standpoint of animal protection. On the other hand, research has been hitherto conducted on numerous macrocyclic compounds having a musk fragrance, in order to conform to the changing odor preference (for example, Non-Patent Documents 1 and 2). However, since synthesis of macrocyclic musk compounds is difficult, and the compounds are highly expensive, only few of them are placed on the market. Therefore, nitro musk compounds represented by musk ketone and musk xylol, and polycyclic musk compounds represented by Galaxolide (registered trademark) and Tonalide (registered trademark) have been exclusively used as musk-based fragrance.

However, from the viewpoint of the increasing inclination toward natural products and environmental concerns of these days, attention is being paid again to macrocyclic musk compounds, which are almost free of problems in view of the direct safety of the compounds themselves, as well as in view of accumulation potential and degradability.

Macrocyclic lactone compounds are being listed as representatives of the macrocyclic musk compounds. However, the macrocyclic lactone compounds available hitherto still cannot be said to be satisfactory in terms of fragrance and cost.

Therefore, development has been desired of macrocyclic musk compounds that satisfy the effectiveness as fragrance materials upon actual preparation of the compounds and the technical and economical problems concomitant with the synthesis of the compounds.

Meanwhile, 14-n-propyloxacyclotetradecan-2-one is known as a macrocyclic lactone compound (Non-Patent Document 3). However, this macrocyclic lactone compound has not been isolated, and it has not known whether the compound indeed has a fragrance, or what kind of fragrance the compound presents.

NON-PATENT DOCUMENT

Non-Patent Document 1: I. B. Bersuker, et al., New J. Chem., Vol. 15, p. 307 (1991)
Non-Patent Document 2: Abe Masami, Perfumes, No. 96, September 1970, p. 19
Non-Patent Document 3: L. Hinkamp, et al., Liebigs Ann. Chem. (1992), 559-563

SUMMARY OF THE INVENTION

1) According to one aspect of the present invention, there is provided a fragrance composition containing, as an active ingredient, a macrocyclic lactone compound represented by the following formula (1):

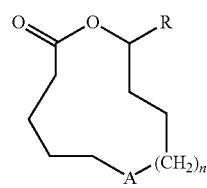

wherein A represents an ethylene group or an ethenylene group; and when A is an ethylene group, R represents an alkyl group having 3 carbon atoms, and n represents an integer from 1 to 6, while when A is an ethenylene group, R represents an alkyl group having 1 to 3 carbon atoms, and n represents an integer from 1 to 6.

2) According to another aspect of the present invention, there is provided a macrocyclic lactone compound represented by the following formula (2):

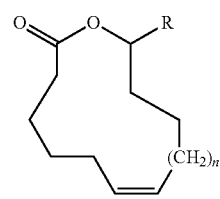

wherein R represents an alkyl group having 1 to 3 carbon atoms, and n represents an integer from 1 to 6.

3) According to still another aspect of the present invention, there is provided use of the macrocyclic lactone compound represented by the formula (1), for the manufacture of the fragrance composition according to the above-mentioned 1).

DETAILED DESCRIPTION OF THE INVENTION

The present invention relates to a fragrance composition having an excellent musky fragrance.

The inventors of the present invention have conducted an investigation on macrocyclic lactone compounds, and they found that the macrocyclic lactone compound represented by the formula (1) shown above has an excellent musky fragrance and thus is useful as a fragrance component. As will be shown in Examples given below, the macrocyclic lactone compound represented by the formula (1) has an excellent musky fragrance. Therefore, the fragrance composition of the present invention is useful as a fragrance component for cosmetics and toiletries, hygiene materials, miscellaneous goods, food products, quasi-medical products, medical products, and the like.

Among these, a macrocyclic lactone compound having a cis-type double bond at the 7-position when numbering starts from the —O— oxygen) as represented by the formula (2), is a novel compound. This novel macrocyclic lactone compound can be produced from a naturally occurring fatty acid in two steps, as will be described in the Examples below, and has an excellent musky fragrance. Therefore, this novel macrocyclic lactone compound is useful as a fragrance component for cosmetics and toiletries, hygiene materials, miscellaneous goods, food products, medical products and the like.

The macrocyclic lactone compound represented by the formula (1) of the present invention has an excellent musky fragrance. Therefore, the fragrance composition of the present invention is useful as a fragrance component for cosmetics and toiletries, hygiene materials, miscellaneous goods, food products, quasi-medical products, medical products and the like.

In the formula (1), when A is an ethenylene group, R may be a methyl group, an ethyl group, an n-propyl group, or an isopropyl group. In view of the fragrance, a methyl group, an ethyl group or an n-propyl group is preferable.

In the formula (1), when A is an ethylene group, R may be an n-propyl group or an isopropyl group. In view of the fragrance, an n-propyl group is preferable.

In the formula (1), n is more preferably an integer from 2 to 5, in view of the fragrance. When R is a methyl group and A is an ethenylene group, n is preferably 5. When R is an ethyl group and A is an ethenylene group, n is preferably 4. When R is an n-propyl group and A is an ethenylene group, n is preferably 3. When R is an n-propyl group and A is an ethylene group, n is preferably 3.

In the formula (1), A may be an ethylene group or an ethenylene group, but A is preferably an ethylene group from the viewpoint of the supply of raw materials.

Specific examples of the macrocyclic lactone compound according to the present invention include 15-methyloxacyclopentadec-7-en-2-one, 16-methyloxacyclohexadec-7-en-2-one, 17-methyloxacycloheptadec-7-en-2-one, 18-methyloxacyclooctadec-7-en-2-one, 14-ethyloxacyclotetradec-7-en-2-one, 15-ethyloxacyclopentadec-7-en-2-one, 16-ethyloxacyclohexadec-7-en-2-one, 17-ethyloxacycloheptadec-7-en-2-one, 13-n-propyloxacyclotridec-7-en-2-one, 14-n-propyloxacyclotetradec-7-en-2-one, 15-n-propyloxacyclopentadec-7-en-2-one, 16-n-propyloxacyclohexadec-7-en-2-one, 14-n-propyloxacyclotetradecan-2-one, and the like. Among these, 16-methyloxacyclohexadec-7-en-2-one, 15-ethyloxacyclopentadec-7-en-2-one, 14-n-propyloxacyclotetradec-7-en-2-one, and 14-n-propyloxacyclotetradecan-2-one are preferable.

The macrocyclic lactone compound represented by the formula (1) has an asymmetric carbon atom at the ω-position of the lactone ring, and thus exists as a mixture of isomers selected from an S-form and an R-form. However, according to the present invention, the lactone compound may be any of these isomeric forms, or may be in a racemic form.

The macrocyclic lactone compound according to the present invention can be produced by a known production method. For example, the macrocyclic lactone compound can be conveniently produced from a fatty acid represented by the formula (3) shown below, according to the following processes (A) and (B).

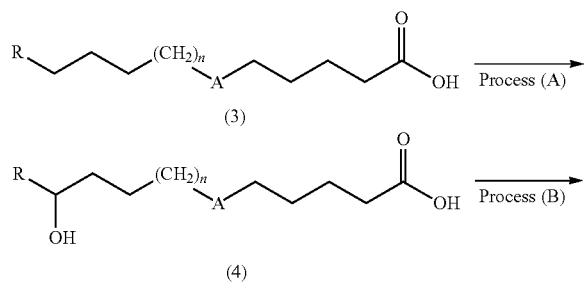

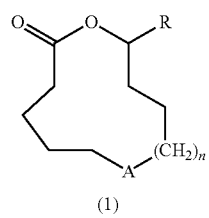

wherein R, A and n have the same meanings as defined above.

The process (A) involves a reaction of obtaining a hydroxy fatty acid represented by formula (4), by subjecting the fatty acid represented by the formula (3) to the action of a biological catalyst including a fatty acid hydroxylase.

The fatty acid represented by the formula (3) may be a saturated fatty acid or an unsaturated fatty acid. This unsaturated fatty acid may be an unsaturated fatty acid having R, A and n that are corresponding to the desired compound represented by the formula (1), and examples thereof include cis-6-dodecenoic acid, cis-6-tridecenoic acid, cis-6-tetradecenoic acid, cis-6-pentadecenoic acid, cis-6-hexadecenoic acid, cis-6-heptadecenoic acid, cis-6-octadecenoic acid, cis-6-nonadecenoic acid, and the like. The saturated fatty acid may be a saturated fatty acid having R, A and n that are corresponding to the desired compound represented by the formula (1), and examples thereof include palmitic acid. These may be used singly or in combination.

The fatty acid represented by the formula (3), which serves as the raw material, can be obtained by a known method (JP-B-2-6516). Particularly, the method for producing cis-6-hexadecenoic acid may involve a method of producing the acid by using a microorganism of the genus *Rhodococcus* (JP-B-4-12718); a method of extracting the acid from Black-eyed Susan vine (*Thunbergia alata*), which is a climber plant; or a method of producing the acid from isopropyl palmitate by using a microorganism of the genus *Rhodococcus* (JP-A-2005-65658). However, the method of producing the acid using a microorganism of the genus *Rhodococcus* is preferable from the viewpoint that cis-6-hexadecenoic acid can be produced in an industrial scale.

In the case of extracting the acid from Black-eyed Susan vine, the whole plant, stalk, flower, leaf or seed of Black-eyed Susan vine is immersed or heated to reflux together with an appropriate extraction solvent, and then the resultant may be appropriately subjected to filtration, concentration, freeze-drying or the like, to thereby obtain a concentrated extract, a dried powder or the like. Examples of the extraction solvent may include the generally-used organic solvents such as methanol, ethanol, propanol, butanol, ether, ethylene glycol, propylene glycol, butylene glycol, petroleum ether, hexane, heptane, cyclohexane, ethyl acetate, acetone, toluene, dichloroethane and chloroform, water, and the like, and these may be used as mixtures of one or more species. The extraction treatment can be carried out according to a conventional method, usually at a temperature of about 3 to 100° C. for several hours to several weeks, and the extract can be used after being purified by gel filtration, column chromatography, precision distillation or the like.

The fatty acid hydroxylase may be an enzyme that hydroxylates the ω-subterminal of a fatty acid. Specific examples of the enzyme include CYP102A1 (P450 BM3), CYP102A2, CYP102A3, CYP102A5, CYP505 and the like, and among these, CYP102A1 is preferable from the viewpoint of reaction yield. These enzymes may be used in combination of plural species.

In the process (A), the biological catalyst may be used in any form, as long as it includes the fatty acid hydroxylases described above. Examples of the biological catalyst containing these enzymes include biological cells such as animal cells or plant cells that produce the enzymes of the present invention, or microbial cells (living cells, dead cells, resting cells, stationary cells or the like), or cultures thereof; organelles (cellular organelles) containing the enzymes of the present invention; homogenates or extracts of the aforementioned biological cells or organelles; crude enzymes; purified enzymes; and the like.

The biological cells and the like that produce the enzymes of the present invention may be naturally-occurring cells, or may be variants modified by various methods including genetic manipulation. These biological catalysts may be used singly, or may be used in combination. Furthermore, the biological catalyst may be used directly, but may also be in a liquid form such as solution or suspension, or in the form of being immobilized on any solid support.

The biological catalyst immobilized on a solid support may be a product obtained by immobilizing the biological catalyst described above on any water-insoluble solid support according to a known method. When the biological catalyst is immobilized on a solid support, recovery and recycling of the catalyst in batch reactions are facilitated, and the biological catalyst can also be used with ease in semi-continuous and continuous reactions. Thus, immobilized biological catalysts that can be used repeatedly for a long term are obtained.

The method of binding the enzyme to a support may be, for example, a physical adsorption method, an ionic bonding method, a covalent bonding method, a crosslinking method, an entrapment method described in Patent Document JP-A-11-192096, or a combination thereof. Examples of the support used in the binding include inorganic materials such as activated carbon, porous glass, acidic white clay, bleached clay, kaolinite, alumina, silica gel, bentonite, hydroxyapatite, calcium phosphate, and metal oxides; naturally-occurring polymers such as starch and gluten; porous synthetic resins; ceramics; ultrafiltration membranes or hollow fibers made of ultrafiltration membranes; butyl- or hexyl-Sephadex having a hydrophobic group; cellulose derivatives having tannin as a ligand; polysaccharides having an ion-exchanging group (DEAE-Sephadex); ion-exchanged resins; natural or synthetic polymer gels or microcapsules; and the like.

In the process (A), an enzyme, a co-enzyme or another substance that accelerates hydroxylation can also be used as necessary, in addition to the fatty acid hydroxylase described above. For example, when NAD(P)H is required, NAD(P)$^+$, as well as glucose dehydrogenase, glucose and the like can be appropriately used. Furthermore, if necessary, heme, 5-aminolevulinic acid, and metal ions ($Fe^{2+}$, $Fe^{3+}$, and the like) can be used according to necessity. The animal cells, plant cells, microbial cells, organelles and the like described above are preferable biological catalysts from the viewpoint that they contain the enzyme family or co-enzyme family needed in hydroxylation.

Production of the hydroxy fatty acid represented by the formula (4) using such a biological catalyst can be carried out under mild conditions as compared with chemical techniques. For example, the pH is usually adjusted to near the optimum pH of enzymes (pH 5 to 9, preferably pH 7 to 8) using a buffer solution. The reaction temperature is from 20 to 60° C., and preferably from 25 to 30° C. The reaction time is from 1 minute to 48 hours, and preferably from 1 to 12 hours.

The reaction system may be added with a surfactant or an organic solvent so as to enhance the solubility of the raw material fatty acid. The surfactant may be a surfactant of nonionic, anionic, cationic or amphoteric type, or the like. As for the organic solvent, any solvent can be used as long as it does not inhibit the enzyme activity and dissolves palmitic acid. Specific examples include polar solvents such as alcohols, ketones and ethers; nitrogen-containing solvents such as pyridine, dimethylformamide, dimethylacetamide and quinoline; sulfur-containing solvents such as dimethylsulfoxide; non-polar solvents such as an aromatic hydrocarbon or a saturated or unsaturated hydrocarbon; and the like. However, acetone is preferred.

In the case of using a biological cell culture as the biological catalyst, for example, the raw material fatty acid can be added to the culture. In regard to the co-enzyme and the like that are needed in the hydroxylation reaction, intracellularly-occurring substances may be used. If necessary, these substances may also be added to the culture. When a culture added with the raw material and appropriate substances is maintained under appropriate culture conditions for a certain time, the enzyme and raw material fatty acid of the present invention in the culture react with each other to produce a hydroxy fatty acid. The appropriate culture conditions and time may vary depending on the type of the cells used, but may be appropriately set according to the conventional knowledge of those ordinarily skilled in the art.

The concentration of the substrate is not particularly limited, but is preferably from 0.001 to 20%, and more preferably 0.05 to 1%. The fatty acid can be added to the reaction system in a batch or continuously.

The hydroxy fatty acid obtained by the process (A) may be isolated by a known method, or may be used in the process (B) without being isolated. However, it is preferable to use the hydroxy fatty acid after isolation.

Separation and recovery of the hydroxy fatty acid represented by the formula (4) from the reaction solutions may be carried out an organic solvents extaction or the like. Aliphatic hydrocarbon-based solvents such as n-hexane; water insoluble organic solvents such as ethyl acetate and chloroform; alcohols such as 2-propanol; and the like can be used for the extraction.

The process (B) involves a reaction of obtaining the macrocyclic lactone compound represented by the formula (1) by subjecting the hydroxy fatty acid represented by the formula (4) to a cyclization reaction.

The hydroxy fatty acid represented by the formula (4) may be an unsaturated hydroxy fatty acid or a saturated hydroxy fatty acid. The unsaturated hydroxy fatty acid is preferably an unsaturated hydroxy fatty acid having a cis-type double bond at the 6-position, and the saturated hydroxy fatty acid is preferably 13-hydroxypalmitic acid.

The unsaturated hydroxy fatty acid having a cis-type double bond at the 6-position may be an unsaturated hydroxy fatty acid having R, A and n that are corresponding to the compound represented by the formula (1), and for example, 11-hydroxy-cis-6-dodecenoic acid;
11-hydroxy-cis-6-tridecenoic acid, 12-hydroxy-cis-6-tridecenoic acid;
11-hydroxy-cis-6-tetradecenoic acid, 12-hydroxy-cis-6-tetradecenoic acid, 13-hydroxy-cis-6-tetradecenoic acid;
12-hydroxy-cis-6-pentadecenoic acid, 13-hydroxy-cis-6-pentadecenoic acid, 14-hydroxy-cis-6-pentadecenoic acid;
13-hydroxy-cis-6-hexadecenoic acid, 14-hydroxy-cis-6-hexadecenoic acid, 15-hydroxy-cis-6-hexadecenoic acid;
14-hydroxy-cis-6-heptadecenoic acid, 15-hydroxy-cis-6-heptadecenoic acid, 16-hydroxy-cis-6-heptadecenoic acid;

15-hydroxy-cis-6-octadecenoic acid, 16-hydroxy-cis-6-octadecenoic acid, 17-hydroxy-cis-6-octadecenoic acid; 16-hydroxy-cis-6-nonadecenoic acid, 17-hydroxy-cis-6-nonadecenoic acid, and 18-hydroxy-cis-6-nonadecenoic acid may be mentioned.

Among these, 11-hydroxy-cis-6-tetradecenoic acid, 12-hydroxy-cis-6-tetradecenoic acid, 13-hydroxy-cis-6-tetradecenoic acid; 12-hydroxy-cis-6-pentadecenoic acid, 13-hydroxy-cis-6-pentadecenoic acid, 14-hydroxy-cis-6-pentadecenoic acid; 13-hydroxy-cis-6-hexadecenoic acid, 14-hydroxy-cis-6-hexadecenoic acid, and 15-hydroxy-cis-6-hexadecenoic acid are preferable, and 13-hydroxy-cis-6-hexadecenoic acid, 14-hydroxy-cis-6-hexadecenoic acid, and 15-hydroxy-cis-6-hexadecenoic acid are more preferable. These unsaturated hydroxy fatty acids can be used singly or in combination.

The process (B) can be carried out either in the presence of a cyclization catalyst or in the absence thereof, as long as the process is carried out under the conventional conditions used in cyclization reactions. The process is preferably carried out in the presence of a cyclization catalyst such as a mixture of dicyclohexylcarbodiimide (hereinafter, also referred to as DCC) and 4-dimethylaminopyridine (hereinafter, also referred to as DMAP) (hereinafter, also referred to as DCC/DMAP); a magnesium compound such as magnesium oxide or magnesium chloride; benzenesulfonic acid, p-toluenesulfonic acid, a carboxylic acid activating reagent (for example, trifluoroacetic anhydride, N,N'-carbonylimidazole, a mixture of di(2-pyridyl)disulfide and triphenylphosphine), a mixture of triphenylphosphine and diethyl azocarboxylate, or sodium t-amylalkoxide. Furthermore, in the case of using DCC/DMAP as a cyclization catalyst, it is preferable to use 4-dimethylaminopyridine hydrochloride (hereinafter, also referred to as DMAP.HCl), in addition to DCC/DMAP.

When DCC/DMAP is used in the process (B), it is preferable to carry out the process in the presence of a solvent. The solvent is not particularly limited, but for example, chloroform and dichloromethane may be mentioned, with chloroform being preferable.

That is, as a specific suitable example of the cyclization reaction, there may be mentioned a method of dissolving the hydroxy fatty acid in a chloroform solution of DCC, DMAP and DMAP.HCl, and heating the solution to reflux (Keck macrolactonization method).

In the case of using DCC/DMAP in the process (B), the amounts of use of DCC, DMAP and DMAP.HCl may be appropriately selected to be amounts that do not cause a delay in the reaction time or a decrease in the rate of reaction, but it is preferable to use the compounds in the amounts of 1.5 to 10 equivalents, 1.5 to 10 equivalents, and 1.5 to 10 equivalents, respectively, based on the hydroxy fatty acid represented by the formula (4).

In the case of using DCC/DMAP in the process (B), the system is usually shaken and stirred for about 10 to 24 hours at 30 to 100° C. The process can be carried out by shaking and stirring the system, preferably for about 15 to 20 hours at 50 to 70° C.

The target compound can be separated by isolating and purifying the compound from the reaction system through an appropriate combination of conventional techniques such as filtration, washing, drying, recrystallization, centrifugation, extraction with various solvents, and chromatography.

The compound of the present invention has an excellent musky fragrance, as will be described in the Examples later. Therefore, the compound of the present invention can be used as an active ingredient of a fragrance composition, and can also be used for the manufacture of a fragrance composition.

The amount of the compound of the present invention incorporated into a fragrance composition is preferably from 0.01 to 50% by weight, and more preferably from 0.1 to 20% by weight, from the viewpoint of the fragrance.

The fragrance composition of the present invention may have the compound of the present invention incorporated alone, but to the extent of not impairing the fragrance of the compound of the present invention, the composition can also have other fragrance substances incorporated together, such as the following: surfactants such as polyoxyethylene lauryl sulfate ether; solvents such as dipropylene glycol, diethyl phthalate, ethylene glycol, propylene glycol, methyl myristate, or triethyl citrate; hydrocarbons such as limonene, α-pinene, β-pinene, terpinene, cedrene, longifolene or valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenylhexanol, 2,2,6-trimethylcyclohexyl-3-hexanol, 1-(2-t-butylcyclohexyloxy)-2-butanol, 4-isopropylcyclohexanemethanol, 4-methyl-2-(2-methylpropyl)tetrahydro-2H-pyran-4-ol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, isocamphylcyclohexanol, or 3,7-dimethyl-7-methoxyoctan-2-ol;

phenols such as eugenol, thymol, or vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate, p-t-butylcyclohexyl acetate, tricyclodecenyl acetate, benzyl acetate, styrallyl acetate, cinnamyl acetate, dimethylbenzylcarbinyl acetate, 3-pentyltetrahydropyran-4-yl acetate, citronellyl propionate, tricyclodecenyl propionate, allyl cyclohexylpropionate, ethyl 2-cyclohexylpropionate, benzyl propionate, citronellyl butyrate, dimethylbenzylcarbinyl n-butyrate, tricyclodecenyl isobutyrate, methyl 2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyl dihydrojasmonate, methyl-2,4-diydroxy-3,6-dimethyl benzoate, ethylmethylphenyl glycidate, methyl anthranilate, or fruitate;

aldehydes such as n-octanal, n-decanal, n-dodecanal, 2-methylundecanal, 10-undecenal, citronellal, citral, hydroxycitronellal, dimethyltetrahydrobenzaldehyde, 4(3)-(4-hydroxy-4-methylpentyl)-3-cyclohexene-1-carboaldehyde, 2-cyclohexylpropanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, or α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-penten-1-yl)-2-cyclopenten-1-one, methylcyclopentenolone, rose ketone, γ-methylionone, α-ionone, carvone, menthone, camphor, nootkatone, benzylacetone, anisylacetone, methyl β-naphthyl ketone, 2,5-dimethyl-4-hydroxy-3(2H)-furanone, maltol, 7-acetyl-1,2,3,4,5,6,7,8-octahydro-1,1,6,7-tetramethylnaphthalene, muscone, civetone, cyclopentadecanone, or cyclohexadecenone;

acetals or ketals, such as acetaldehyde ethylphenylpropyl acetal, citral diethylacetal, phenylacetaldehyde glycerinacetal, or ethyl acetoacetate ethylene glycol ketal; ethers such as anethole, β-naphthyl methyl ether, β-naphthyl ethyl ether, limonene oxide, rose oxide, 1,8-cineole, or racemic or optically active dodecahydro-3a,6,6,9a-tetramethylnaphtho[2,1-b]furan; nitriles such as citronellylnitrile;

lactones other than the compound of the present invention, such as γ-nonalactone, γ-undecalactone, δ-decalactone, γ-jasmolactone, coumarin, cyclopentadecanolide, cyclohexadecanolide, ambrettolide, ethylene brassylate, or 11-oxahexadecanolide; other fragrance substances including a natural essence oil or a natural extract, such as orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, cypress, vetiver, patchouli, or labdanum; and the like. These other components may be incorporated singly or as a mixture of plural species.

For the purpose of imparting an excellent odor of high preference, or improving the odor of an object mixture, the macrocyclic lactone compound represented by the formula (1) can be used as a fragrance component in various products such as cosmetics and toiletries, hygiene materials, miscellaneous goods, food products, quasi-medical products and medical products.

For example, the macrocyclic lactone compound of the present invention can be used as a fragrance component in fragrance products such as perfumes and colognes; shampoos, hair rinses, hair tonics, hair creams, mousses, gels, pomades, sprays and other hair cosmetics; skin cosmetic materials such as lotions, essences, creams, emulsions, packs, foundations, powders, lipsticks, and various make-up products; soaps, dishwashing detergents, laundry detergents, softeners, disinfecting detergents, deodorizing detergents, room fragrances, furniture cares, glass cleaners, furniture cleaners, floor cleaners, disinfectants, pesticides, bleaches, and other various hygiene detergents; toothpastes; quasi-medical products such as mouth washers, bath agents, antiperspirants, and permanent wave solutions; miscellaneous goods such as toilet papers and tissue papers; medical products; food products; and the like.

The amount of incorporation of the perfume composition of the present invention into products is preferably from 0.001 to 50% by weight, and more preferably from 0.01 to 20% by weight, in terms of the macrocyclic lactone compound represented by the formula (1).

EXAMPLES

Hereinafter, the present invention will be described in detail by way of Examples.

Reference Example 1

Expression of P450 BM3

(i) Construction of *Escherichia coli* Co-Expressing P450 BM3 and GDH

*Escherichia coli* BL21Star (DE3) (manufactured by Invitrogen, Inc.) was used as a host for protein production. pET21a (manufactured by Novagene, Inc.) was used as a plasmid for high expression vector. *E. coli* strain HB101 (manufactured by Takara Bio, Inc.) was used as an *E. coli* host used for the subcloning of genes.

*Bacillus megaterium* strain ATCC 14581 was used as a gene source for P450 BM3 (SEQ ID NO:1). *Bacillus subtilis* strain 168 (ATCC 23857) was used as a gene source of glucosedehydrogenase (GDH) (SEQ ID NO:2).

pETBM3-gdh is a vector that highly expresses P450 BM3 and GDH. This pETBM3-gdh was constructed by inserting BM3 gene into a multi-cloning site of pET21a, and then inserting GDH gene to a site downstream to the BM3 gene. The amplification of the BM3 gene was carried out using the genome of *B. megaterium* strain ATCC 14581 as a template, and using BM3/BamHI FW and BM3/EcoRI RV as primers (SEQ ID NOs:3 and 4). Pyrobest DNA polymerase (manufactured by Takara Bio, Inc.) was used in the PCR process. The composition and reaction conditions for the PCR were set according to the appended protocol.

The amplified DNA fragment of about 3.2 kbp in length was treated with Bam HI and Eco RI, and was inserted to the sites of Bam HI and Eco RI of pET21a, to thereby construct pETBM3. The amplification of GDH gene was carried out using the genome of *B. subtilis* strain 168 as a template, and using BSgdh/EcoRI f1 and BSgdh/Xho I r1 (SEQ ID NOs:5 and 6) as primers. The amplified DNA fragment of about 0.8 kbp in length was treated with Eco RI and Xho I, and was inserted to the sites of Eco RI and Xho I of pETBM3, to thereby construct pETBM3-gdh.

As for the verification of gene sequence, ABI PRISMT™ 3100 Genetic Analyzer (manufactured by Applied Biosystems, Inc.) was used as a DNA sequence analyzer, and a sample was prepared according to the appended protocol, using Big Dye™ Terminator v3.1 Cycle Sequencing Ready Reaction (manufactured by Applied Biosystems, Inc.), and using the plasmid as a template.

The constructed expression vector was introduced into *E. coli* by a competent cell method. An appropriate amount of plasmid DNA was added to 40 μL of *E. coli* HB101 competent cells or 40 μL of *E. coli* BL21 Star (DE3) competent cell, which had been thawed on ice, and the mixture was incubated for 30 minutes on ice. The mixture was incubated at 42° C. for 45 seconds, and was immediately placed on ice to stand still for 2 minutes. 360 μL of SOC medium (manufactured by Takara Bio, Inc.), which had been previously incubated at 37° C., was added to the mixture, and the mixture was shaken for 60 minutes at 150 rpm at 37° C. The each transformation liquid was plated onto a LB plate containing 100 ppm of ampicillin sodium salt, and the plates were incubated for 16 hours at 37° C. The thus grown bacterium was separated as a transformant.

The separated transformant was inoculated by streaking on LB plates, and then was incubated for 16 hours at 30° C. The grown bacterium was suspended in 0.5 mL of sterilized 20% glycerol, and then the suspension was stored frozen at –80° C. to be used as freeze-stored bacterial cells.

(ii) Expression of Target Protein, and Preparation of Enzyme Solution

Growth conditions of *E. coli* and expression of protein were carried out as follows. Transformants were picked and cultured for 8 hours at 37° C. and 250 rpm in 5 mL LB medium containing 100 ppm of ampicillin sodium salt. 1 mL of these cultures were used to inoculate fresh LB medium containing 100 ppm of ampicillin sodium salt. The resultant was cultured at 37° C. and 120 rpm, until OD600 reached about 0.4 (for about 2.5 hours). The culture was induced by adding 0.5 mM of IPTG, 1 mM of 5-aminolevulinic acid and 0.001% of $FeCl_3.6H_2O$ (as final concentrations), and was incubated for 16 hours at 25° C. The reagents were all filtered before use. The culture was centrifuged for 10 minutes at 8000 rpm to harvest the bacterial cells, and the cells were washed once with a 50 mM Tris-HCl buffer (pH 8.0).

The bacterial cells recovered from 100 mL of the culture were suspended in 2 mL of a 50 mM Tris-HCl (pH 8.0), containing one tablet of Complete EDTA Free (manufactured by Roche, Ltd.) per 50 mL. The bacterial suspension was fed into Lysing Matrix B (manufactured by Q-Biogene, Inc.), and the bacterial cells were disrupted using FastPrep (manufactured by Q-Biogene, Inc.) following the appended protocol. If the culture had exceeded 1 L, the bacterial cell suspension was prepared at a similar proportion as described above, and the suspension was passed once through a FRENCH PRESS (manufactured by Thermo Spectronic Co.) at a rate of 100 droplets/minute at 15000 psi. The disrupted cell fluid was centrifuged for 10 minutes at 15000 rpm, and the supernatant was collected. An equal amount of glycerol was added to the supernatant, and the mixture was stored at −30° C. This stored fluid was used as an enzyme solution.

Example 1

Hydroxylation Reaction of Fatty Acid

Hydroxylation of palmitic acid (manufactured by Sigma-Aldrich Company, purity 99%) was attempted using the enzyme solution prepared as described in Reference Example 1. The enzymatic reaction was carried out as follows.

Thirty sets of 200 mL reaction liquids were prepared in 500-mL Sakaguchi flasks, so as to contain a 100 mM potassium phosphate buffer (pH 8.0), 0.5 g/L of palmitic acid, 5 mM of glucose and 50 mL/L of the bacterial cell extract, all as final concentrations, and the reaction liquids were incubated for 2 minutes at 25° C. To each of the incubated solutions, $NADP^+$ was added to a final concentration of 0.05 mM, and the solution was incubated for 14 hours at 25° C. and 120 rpm. 2% (v/v) concentrated hydrochloric acid was added to the reaction liquid, then the mixture was extracted with 50% (v/v) hexane. The extract was dried up by vacuum during, and thus 1.70 g of a hexane extract was obtained. The hydroxyl fatty acid contained in the hexane extract was methylated with Boron trifluoride-methanol solution 14% in methanol(manufactured by Wako chemical), and then was trimethylsilylated with N-trimethylsilimidazole (manufactured by Wako chemical).

1 µL of this solution was analyzed on a capillary gas chromatograph-mass spectrometer (HP 6890/5973 GC-MS (manufactured by Agilent, Inc.)) using a 30 m×200 µm0.25 µm DB-1 MS (manufactured by J&W Scientific, Inc.). The analysis was carried out using high purity helium for the mobile phase, at a flow rate of 1 mL/min. The temperature program used was 100° C. for 1 minute, a temperature gradient of 20° C./minute to 300° C., and isothermic at 300° C. for 5 minutes. 16-Hydroxypalmitic acid was used as a standard for the hydroxy fatty acid.

13-Hydroxypalmitic acid was obtained, and the reaction yield was 0.8%.

The total amount of 13-hydroxypalmitic acid, 14-hydroxypalmitic acid and 15-hydroxypalmitic acid was 120 mg, and the ratio of hydroxylation position was ω-1 position: 32.9%, ω-2 position: 47.1%, and ω-3 position: 20.0%, respectively.

Example 2

Intramolecular Cyclization of Hydroxy Fatty Acid 2.72 g of dicyclohexylcarbodiimide, 2.42 g of 4-dimethylaminopyridine, 2.09 g of 4-dimethylaminopyridine hydrochloride were added in 294.92 g of chloroform. 1.70 g of the product obtained in Example 1 in 39.6 mL of THF was added dropwise into the chloroform solution over 16 hours using a syringe pump under reflux. The mixture was stirred for 30 minutes under reflux, and then was cooled to room temperature. The solvent was distilled off under reduced pressure, and then the residue was diluted with diethyl ether. Insoluble matters were separated by filtration.

2.77 g of a crude product was obtained by vacuum distillation of the filtrated solvent. The crude product was purified by column chromatography (silica gel; 1.6% THF-hexane), and thus 0.98 g of a lactonization product (total purity of isomers 4.8%).

Example 3

Structure Confirmation of Macrocyclic Lactone Compound and Sensory Evaluation Because the obtained product contained impurities such as dicyclohexylcarbodiimide, the macrocyclic lactone compound was separated by preparative gas chromatography.

First, 0.1 g of the product obtained in Example 2 was prepared into an ethanol solution at a concentration of 10%, and 5 µL of the solution was injected by splitless injection, to thereby obtain a chromatogram. After the injection, the main product was introduced into a preparative fraction collector (manufactured by Gerstel GmbH) only for it's retention time, and this operation was repeated 80 times to obtain a concentrate of the main component. This concentrate was eluted with 0.5 ml of ethanol, and three components were respectively isolated by conventional gas chromatography, at proportions of 7.3%, 53.9% and 38.8% in an order of increasing retention time. The three components were then identified by mass fragmentation, as 14-n-propyloxacyclotetradecan-2-one, 15-ethyloxacyclopentadecan-2-one, and 16-methyloxacyclohexadecan-2-one. It was confirmed by a sensory evaluation that the mixture of the three components has a luxurious and beautiful musk fragrance that suggests a musk tincture. The invented product is characterized by having a strong sweet scent as compared with commercially available cyclohexadecanolide, which has the same molecular weight, and therefore, it is speculated that branched alkyl groups bring an odor which is closer to the natural odor presented by muscone.

It was also confirmed by sniffing gas chromatography (GC-Olfactometry) that 14-n-propyloxacyclotetradecan-2-one has a musk fragrance.

16-Methyloxacyclohexadecan-2-one

MS; 254(4, $M^+$), 237(10, $M^+$-$CH_3$), 236(51, $M^+$-$H_2O$), 210(27, $M^+$-$HCOCH_3$), 98(48), 97(61), 96(44), 84(41), 83(59), 69(64), 55(100), 41(66)

15-Ethyloxacyclopentadecan-2-one

MS; 254(4, $M^+$), 236(47, $M^+$-$H_2O$), 225(41, $M^+$-$C_2H_5$), 196(29, $M^+$-$HCOC_2H_5$), 98(48), 97(66), 96(41), 95(42), 83(60), 69(68), 55(100), 41(69)

14-n-propyloxacyclotetradecan-2-one

MS; 254(3, $M^+$), 236(41, $M^+$-$H_2O$), 211(55, $M^+$-$C_3H_7$), 182(46, $M^+$-$HCOC_3H_7$), 111(41), 98(63), 97(53), 83(57), 69(52), 55(100), 43(46), 41(72)

Example 4

Fragrance Composition for Fabric Detergent 85 parts by weight of a fragrance composition having the composition indicated in Table 1 was added with 15 parts by weight of the lactonization product obtained in Example 2, and thus a fragrance composition for fabric detergent characterized by having a smooth musk fragrance with a sense of flower-like freshness, could be obtained.

TABLE 1

| Incorporated component | Parts by weight |
|---|---|
| Methyl dihydrojasmonate | 20 |
| β-Phenylethyl alcohol | 10 |
| 4-Methyl-2-(2-methylpropyl)tetrahydro-2H-pyran-4-ol | 8 |
| Rose type combined perfume | 8 |
| 7-Acetyl-1,2,3,4,5,6,7,8-octahydro-1,1,6,7-tetramethylnaphthalene | 8 |
| cis-3-Hexenyl salicylate | 5 |
| Dihydromyrcenol | 5 |
| p-t-Butylcyclohexyl acetate | 5 |

TABLE 1-continued

| Incorporated component | Parts by weight |
|---|---|
| Terpineol | 4 |
| 4-Isopropylcyclohexanemethanol | 4 |
| 1-(2-t-Butylcyclohexyloxy)-2-butanol | 4 |
| 2-Methyl-4-(2,2,3-trimethyl-3-cyclopenten-1-yl)-2-buten-1-ol | 2 |
| γ-Undecalactone | 1 |
| Dodecahydro-3a,6,6,9a-tetramethylnaphtho[2,1-b]furan | 1 |
| Total | 85 |

Example 5

Hydroxylation Reaction of cis-6-hexadecenoic Acid

Hydroxylation of cis-6-hexadecenoic acid was carried out using the enzyme solution prepared as described in Reference Example 1. The cis-6-hexadecenoic acid used in this reaction was a product prepared by a fermentation production using *Rhodococcus* sp. strain KSM-T645 (P-18182) and purification according to the method described in a prior art document (Non-Patent Document: Biosci. Biotechnol. Biochem. (2000) 64, 1064). The enzymatic reaction was carried out as follows, using the purified cis-6-hexadecenoic acid (purity 93.3%, calculated based on GC peak ratio).

Fifteen sets of 200 mL reaction liquids were prepared in 500-mL Sakaguchi flasks, so as to contain a 100 mM potassium phosphate buffer (pH 8.0), 0.5 g/L of cis-6-hexadecenoic acid, 5 mM of glucose and 50 mL/L of the bacterial cell extract, all as final concentrations, and the reaction liquids were incubated for 2 minutes at 25° C. To each of the incubated solutions, $NADP^+$ was added to a final concentration of 0.05 mM, and the solution was incubated for 14 hours at 25° C. and 120 rpm. 2% (v/v) concentrated hydrochloric acid was added to the reaction liquid, then the mixture was extracted with 50% (v/v) hexane. The extract thus obtained was dried up by vacuum drying, and thus 1.02 g of a hexane extract was obtained. The hydroxyl fatty acid contained in the hexane extract was methylated with Boron trifluoride-methanol solution 14% in methanol, and then was trimethylsilated with N-trimethylsilylimidazole.

1 μL of this solution was analyzed on the GC-MS as above in Example 1.

The total amount of 15-hydroxy-6-hexadecenoic acid, 14-hydroxy-6-hexadecenoic acid and 13-hydroxy-6-hexadecenoic acid obtained by the reaction was 460 mg, and the ratio was such that 15-hydroxy-6-hexadecenoic acid: 51.3%, 14-hydroxy-6-hexadecenoic acid: 35.5%, and 13-hydroxy-6-hexadecenoic acid: 13.2%, respectively.

Example 6

Intramolecular Cyclization of Hydroxy Fatty Acid 1.58 g of dicyclohexylcarbodiimide, 1.40 g of 4-dimethylaminopyridine, and 1.21 g of 4-dimethylaminopyridine hydrochloride were added in 170.91 g of chloroform. 1.00 g of the product obtained in Example 5 in 23.0 mL of THF was added dropwise into the chloroform solution over 15 hours using a syringe pump under reflux. After completion of the dropwise addition, the mixture was stirred for 30 minutes under reflux, and then was cooled to room temperature. The solvent was distilled off under reduced pressure, and then the residue was diluted with diethyl ether. Insoluble matters were separated by filtration.

3.07 g of a crude product was obtained by vacuum distillation of the filtrated solvent. The crude product was purified by column chromatography (silica gel; 1.6% THF-hexane), and thus 0.89 g of a lactonization product (total purity of isomers 47.6%).

Example 7

Structure Confirmation of Novel Macrocyclic Lactone Compound and Sensory Evaluation Because the obtained product contained impurities such as dicyclohexylcarbodiimide, the macrocyclic lactone compound was separated by preparative gas chromatography.

First, 0.08 g of the product obtained in Example 6 was prepared into an ethanol solution at a concentration of 10%, and 5 μL of the solution was injected by splitless injection, to thereby obtain a chromatogram. After the injection, the main product was introduced into a preparative fraction collector (manufactured by Gerstel GmbH) only for it's retention time, and this operation was repeated 80 times to obtain a concentrate of the main component. This concentrate was eluted with 0.1 ml of ethanol, and a mixture of three components obtained by conventional gas chromatography, at proportions of 48% (two components overlapping) and 52% in an order of increasing retention time. The three components were then identified by mass fragmentation, as 14-n-propyloxacyclotetradec-7-en-2-one, 15-ethyloxacyclopentadec-7-en-2-one, and 16-methyloxacyclohexadec-7-en-2-one. It was also confirmed by an evaluation that the mixture of the three components has a musk fragrance with sweetness that suggests cyclopentadecenolide.

It was also confirmed by sniffing gas chromatography (GC-Olfactometry) that each of the three components had a musk fragrance. The three components were novel compounds.

The mass fragmentation data of the obtained novel macrocyclic lactone compounds are presented below.

16-Methyloxacyclohexadec-7-en-2-one

MS; 252(45, $M^+$), 237(4), 234(2), 96(71), 95(78), 94(44), 82(88), 81(100), 80(75), 67(88), 55(70), 41(62)

15-Ethyloxacyclopentadec-7-en-2-one

MS; 252(38, $M^+$), 234(2), 223(9), 96(66), 95(78), 94(46), 82(85), 81(100), 80(69), 79(41), 67(90), 55(71), 41(61)

SEQUENCE LISTING

What is claimed is:

1. A fragrance composition comprising, as an active ingredient, a macrocyclic lactone compound represented by the following formula (1):

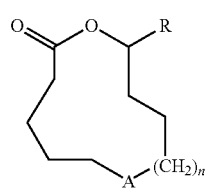

wherein A represents an ethylene group or an ethenylene group; and when A is an ethylene group, R represents an alkyl group having 3 carbon atoms, and n represents an integer from 1 to 6, while when A is an ethenylene group, R represents an alkyl group having 1 to 3 carbon atoms, and n represents an integer from 1 to 6.

2. The fragrance composition according to claim 1, wherein R is a methyl group, A is an ethenylene group, and n is 5; R is an ethyl group, A is an ethenylene group, and n is 4; or R is an n-propyl group, A is an ethenylene group, and n is 3.

3. The fragrance composition according to claim 1, wherein the macrocyclic lactone compound represented by the formula (1) is 14-n-propyloxacyclotetradecan-2-one.

4. The fragrance composition according to claim 3, wherein the content of 14-n-propyloxacyclotetradecan-2-one is from 0.01 to 50% by weight based on the total composition.

5. A macrocyclic lactone compound represented by the following formula (2):

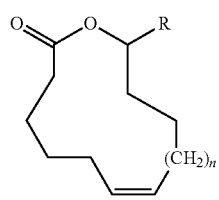

wherein R represents an alkyl group having 1 to 3 carbon atoms, and n represents an integer from 1 to 6.

6. The macrocyclic lactone compound according to claim 5, wherein R is a methyl group, and n is 5; R is an ethyl group, and n is 4; or R is an n-propyl group, and n is 3.

7. A fragrance composition comprising, as an active component, a macrocyclic lactone compound according to claim 6 in an amount of 0.01% to 50% by weight.

* * * * *